United States Patent [19]

Goeders

[11] Patent Number: 5,869,474
[45] Date of Patent: *Feb. 9, 1999

[54] LOW DOSAGE TREATMENT FOR COCAINE CRAVING AND WITHDRAWAL

[75] Inventor: Nicholas E. Goeders, Shreveport, La.

[73] Assignee: Board of Supervisors of Louisiana State University and Agricultural and Mechanical College, Baton Rouge, La.

[*] Notice: This patent issued on a continued prosecution application filed under 37 CFR 1.53(d), and is subject to the twenty year patent term provisions of 35 U.S.C. 154(a)(2).

[21] Appl. No.: 857,376

[22] Filed: May 16, 1997

[51] Int. Cl.$^6$ .......................... A61K 31/50; A61K 31/56; A61K 31/495

[52] U.S. Cl. .......................... 514/171; 514/252; 514/327; 514/382; 514/396; 514/812

[58] Field of Search .................................... 514/171, 252, 514/327, 382, 396, 812

[56] References Cited

U.S. PATENT DOCUMENTS

| | | | |
|---|---|---|---|
| 4,661,493 | 4/1987 | Gibbs | 514/252 |
| 4,814,333 | 3/1989 | Ravaris | 514/255 |
| 4,942,162 | 7/1990 | Rosenburg et al. | 514/252 |
| 5,456,850 | 10/1995 | Liu et al. | 252/106 |

OTHER PUBLICATIONS

Goeders et al., "Effects of Ketoconazole on Intravenous Cocaine Self–Administration in Rats," an abstract submitted to the Fifty–Eighth Annual Scientific Meeting of the College on Problems of Drug Dependence (CPDD), Jun. 22–27, 1996.

H.D. Kleber, "Pharmacotherapy, Current and Potential, for the Treatment of Cocaine Dependence," Clinical Neuropharmacology, vol. 18, Suppl. 1, pp. S96–S109 (1995).

Di Paolo et al., "Endocrine and Neurochemical Actions of Cocaine," Canadian Journal of Physiology and Pharmacology, vol. 67, pp. 1177–1181 (1989).

Joels et al., "Mineralocorticoid and Glucocorticoid Receptors in the Brain. Implications for Ion Permeability and Transmitter Systems," Progress in Neurobiology, vol. 43, pp. 1–36 (1994).

Baumann et al., "Effects of Intravenous Cocaine on Plasma Cortisol and Prolactin in Human Cocaine Abusers," Biological Psychiatry, vol. 38, pp. 751–755 (1995).

Mendelson et al., "Buprenorphine Attenuates the Effects of Cocaine on Adrenocorticotropin (ACTH) Secretion and Mood States in Man," Neuropsychopharmacology, vol. 7, No. 2,, pp. 157–162 (1992).

Heesch et al., "Effects of Cocaine on Cortisol Secretion in Humans," American Journal of the Medical Sciences, vol. 310, No. 2, pp. 61–64 (1995).

Gawin et al., "Cocaine Dependence," Annual Review of Medicine, vol. 40, pp. 149–161 (1989).

Goeders et al., "Non–contingent Electric Footshock Facilitates the Acquisition of Intravenous Cocaine Self–Administration in Rats," Psychopharmacology, vol. 114, pp. 63–70 (1994).

Goeders et al., "Role of Corticosterone in Intravenous Cocaine Self–Administration in Rats," Neuroendocrinology vol. 64, pp. 337–348 (1996).

Goeders et al., "Effects of Surgical and Pharmacological Adrenalectomy on the Initiation and Maintenance of Intravenous Cocaine Self–Administration in Rats," Brain Research, vol. 722, pp. 145–152 (1996). Inhibition of.

Piazza et al., "Inhibition of Corticosterone Synthesis by Metyrapone Decreases Cocaine–Induced Locomotion and Relapse of Cocaine Self–Administration," Brain Research, vol. 658, pp. 259–264 (1994).

N. Sonino, "The Use of Ketoconazole as an Inhibitor of Steroid Production," New England Journal of Medicine, vol. 317 (No. 13), pp. 812–818 (1987).

Engelhardt et al., "Ketoconazole Blocks Cortisol Secretion in Man by Inhibition of Adrenal 11β–Hydrolase," Klin. Wochenschr., vol. 63, pp. 607–612 (1985).

Ghadirian et al., The Psychotropic Effects of Inhibitors of Steroid Biosynthesis in Depressed Patients Refractory to Treatment, Biological Psychiatry, vol. 37, pp. 369–375 (1995).

Wolkowitz et al., "Ketoconazole Administration in Hypercortisolemic Depression," American Journal of Psychiatry, vol. 150, pp. 810–812 (1993).

Goeders et al., "Ketoconazole Reduces Intravenous Cocaine Self–Administration in Rats," submitted for publication in Psychopharmacology (1997).

*Primary Examiner*—Leonard Schenkman
*Attorney, Agent, or Firm*—Bonnie J. Davis; John H. Runnels

[57] ABSTRACT

Ketoconazole is used for treating cocaine addiction. Mammals, including humans, that are chronically addicted to cocaine are treated with ketoconazole to decrease self-administration of the drug.

20 Claims, 5 Drawing Sheets

LOW DOSAGE TREATMENT FOR COCAINE CRAVING AND WITHDRAWAL

The development of this invention was partially funded by the Government under Public Health Service Grant RO1 DA06013 from the National Institute on Drug Abuse. The Government may have certain rights in this invention.

This invention pertains to the use of low dosages of ketoconazole to decrease self-administration of cocaine in mammals, particularly humans, with cocaine dependency, without a substantial decrease in normal locomotor activity.

Cocaine is used primarily for the pleasure and euphoria it produces. Many people continue to use the drug despite severe penalties associated with its possession and sale. It is estimated that more than 22 million people in the United States have tried cocaine at least once. The medical, social, economic, and legal problems associated with non-medical use of the drug will likely not be mitigated simply through increased drug enforcement interventions and more stringent prison sentences. The cocaine epidemic will likely be curtailed only through a decrease in the demand for the drug. Achieving a decrease would require both increased education, before drug use starts as well as during treatment; and the establishment of more efficient, effective, and accessible drug treatment programs.

Current programs for treating cocaine addiction have produced disappointing results. Treatment-seeking addicts often refuse or discontinue treatment with conventional medications because of undesirable side effects. There is a need for new pharmacotherapies that are more specific for cocaine treatment. The primary goal of these pharmacotherapies is to provide a "window of opportunity" during which drug-taking is suppressed, thereby permitting the use of relapse-prevention and other nonpharmacological methods. See H. D. Kleber, "Pharmacotherapy, Current and Potential, for the Treatment of Cocaine Dependence," Clinical Neuropharmacology, vol. 18, Suppl. 1, pp. S96–S109 (1995).

The neurobiological actions of cocaine include effects on neuroendocrine and neuropeptide systems thought to affect stress and anxiety in humans. Di Paolo et al., "Endocrine and Neurochemical Actions of Cocaine," Canadian Journal of Physiology and Pharmacology, vol. 67, pp. 1177–1181 (1989). A relationship has been reported between cocaine use and the activation of the hypothalamo-pituitary-adrenal ("HPA") axis. In mammals, this activation results in increased levels of adrenocorticosteriods, both mineralocorticoids and glucocorticoids. These hormones affect various body cell functions, including communication between brain cells. The steroids bind to intracellular receptors in the brain, causing slow effects that involve gene transcription. The steroids may also evoke rapid effects via membrane receptors. Within the mammalian brain, there are at least two subtypes of intracellular receptors. Mineralocorticoid receptors (Type I) bind with equal affinity both to aldosterone, a mineralocorticoid, and to corticosterone, a glucocorticoid. The glucocorticoid receptor (Type II) binds with greater affinity to corticosterone than to aldosterone by an order of magnitude. See Joëls et al., "Mineralocorticoid and Glucocorticoid Receptors in the Brain. Implications for Ion Permeability and Transmitter Systems," Progress in Neurobiology, vol. 43, pp. 1–36 (1994).

Cocaine is known to affect the concentration of glucocorticoids. The glucocorticoid with the highest concentration in the plasma differs among species of mammals. For example, corticosterone is the primary plasma glucocorticoid in rats, while cortisol is the primary plasma glucocorticoid in humans. The acute, intravenous administration of cocaine increases the secretion of cortisol and adrenocorticotropin (ACTH) in chronic cocaine users. Baumann et al., "Effects of Intravenous Cocaine on Plasma Cortisol and Prolactin in Human Cocaine Abusers," Biological Psychiatry, vol. 38, pp. 751–755 (1995), discloses that acute cocaine administration significantly elevated plasma cortisol, but did not affect prolactin in human cocaine users, suggesting that cocaine activates the HPA axis in humans. Mendelson et al., "Buprenorphine Attenuates the Effects of Cocaine on Adrenocorticotropin (ACTH) Secretion and Mood States in Man," Neuropsychopharmacology, vol. 7, no. 2, pp. 157–162 (1992) discloses that buprenorphine suppression of cocaine self-administration may be due, in part, to suppression of cocaine-induced increases in plasma ACTH levels and concomitant subjective reports of euphoria. The intranasal administration of cocaine increases cortisol secretion in male volunteers without a history of drug abuse. Heesch et al., "Effects of Cocaine on Cortisol Secretion in Humans," American Journal of the Medical Sciences, vol. 310, no. 2, pp. 61–64 (1995).

Clinical evidence supports the conclusion that the HPA axis is involved in the etiology of cocaine use and withdrawal. For example, initial cocaine use has been reported to produce profound subjective feelings of well-being and a decrease in anxiety in humans. However, some of the major symptoms observed during withdrawal from chronic cocaine intoxication include severe anxiety, as well as restlessness, agitation, and depression. Gawin et al., "Cocaine Dependence," Annual Review of Medicine, vol. 40, pp. 149–161 (1989).

Preclinical research in rodents has suggested that stress and the HPA axis play an important role in cocaine reinforcement. In particular, exposure to environmental stress (e.g., social isolation, restraint, electric footshock, tail pinch) makes rats more sensitive or more vulnerable to self-administering cocaine or amphetamine. Goeders et al., "Non-contingent Electric Footshock Facilitates the Acquisition of Intravenous Cocaine Self-Administration in Rats," Psychopharmacology, vol. 114, pp. 63–70 (1994). In other words, exposure to stress will cause rats to self-administer a psychostimulant drug at lower concentrations of the drug, suggesting that stress sensitized the rats to the reinforcing effects of these drugs. Rates of self-administration are significantly correlated with plasma corticosterone levels; increased cocaine self-administration is directly related to stress-induced increases in plasma corticosterone. Goeders et al., "Role of Corticosterone in Intravenous Cocaine Self-Administration in Rats," Neuroendocrinology, vol. 64, pp. 337–348 (1996). In addition, bilateral adrenalectomy completely abolished the acquisition of intravenous cocaine self-administration in rats, suggesting that corticosterone may be necessary for cocaine reward. Goeders et al., "Effects of Surgical and Pharmacological Adrenalectomy on the Initiation and Maintenance of Intravenous Cocaine Self-Administration in Rats," Brain Research, vol. 722, pp. 145–152 (1996). Inhibition of corticosterone synthesis with metyrapone also attenuated ongoing cocaine self-administration, suggesting that corticosterone may be necessary for the initiation as well as the maintenance of cocaine self-administration. See also, Piazza et al., "Inhibition of Corticosterone Synthesis by Metyrapone Decreases Cocaine-Induced Locomotion and Relapse of Cocaine Self-Administration," Brain Research, vol. 658, pp. 259–264 (1994).

Ketoconazole has previously been used as an antifungal agent with a broad spectrum of activity and low toxicity. Ketoconazole is currently approved by the FDA for use in humans in the treatment of several fungal diseases. This drug inhibits the 11β-hydroxylation and 18-hydroxylation steps in the synthesis of adrenocorticosteroid, and also functions as a glucocorticoid (Type II) receptor antagonist. See N. Sonino, "The Use of Ketoconazole as an Inhibitor of Steroid Production," New England Journal of Medicine, vol. 317 (No. 13), pp. 812–818 (1987); and Engelhardt et al., "Ketoconazole Blocks Cortisol Secretion in Man by Inhibition of Adrenal 11β-Hydrolase," Klin. Wochenschr., vol. 63, pp. 607–612 (1985).

Recent clinical trials have suggested that ketoconazole is also effective in the treatment of hypercortisolemic depression that is resistant to standard antidepressant therapy. Other imidazole drugs are known to inhibit adrenal cortisol synthesis, for example, etomidate, clotrimazole, aminoglutethimide, and analogs thereof. See U.S. Pat. No. 4,814,333. Ghadirian et al., "The Psychotropic Effects of Inhibitors of Steroid Biosynthesis in Depressed Patients Refractory to Treatment, Biological Psychiatry, vol. 37, pp. 369–375 (1995), discloses improvement in the depressed mental state upon treatment with aminoglutethimide (250 to 800 mg/day), ketoconazole (400 to 1200 mg/day), or a combination of either of these with metyrapone (250 to 1000 mg/day). Wolkowitz et al., "Ketoconazole Administration in Hypercortisolemic Depression," American Journal of Psychiatry, vol. 150, pp. 810–812 (1993), discloses that administration of ketoconazole (400 to 800 mg/day) decreased the serum cortisol level and decreased the measured state of depression.

U.S. Pat. No. 4,814,333 discloses that ketoconazole lowers depression at doses of 200 to 800 mg/day (or a maximum of 8 mg/kg of body weight) in patients with hypercortisolemia by inhibiting synthesis of cortisol in the adrenal cortex.

U.S. Pat. No. 5,456,851 discloses that shampoo containing ketoconazole is useful for the treatment of scaling due to dandruff.

U.S. Pat. No. 4,942,162 discloses that topical application of ketoconazole is useful for treating psoriasis and seborrheic dermatitis.

U.S. Pat. No. 4,661,493 discloses that ketoconazole is useful in treating vaginal Herpes virus infections.

I have discovered that treatment with low dosages of ketoconazole decreases intravenous cocaine self-administration in mammals. Without wishing to be bound by this theory, I believe that ketoconazole is effective at lower doses than other inhibitors of glucocorticoid synthesis because it also acts as an antagonist to corticosterone at glucocorticoid (Type II) receptors, and that these receptors are responsible in part for sensitivity to cocaine. For example, ketoconazole is therapeutically effective at a dose that is an order of magnitude lower, on a molar basis, than a therapeutically effective dose of metyrapone.

Figure 1:
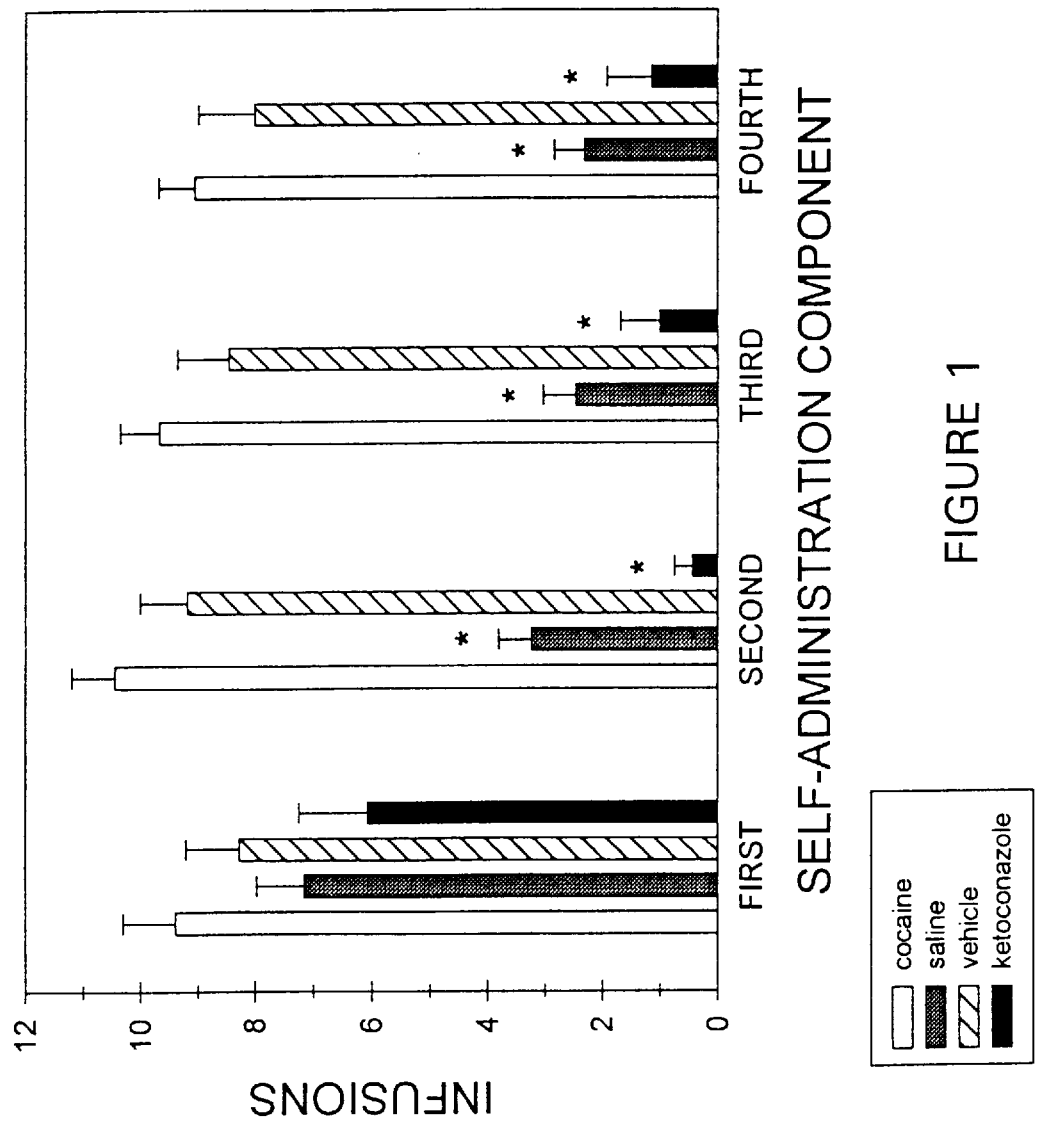
FIG. 1 illustrates the effects of various treatments on the number of self-administered infusions delivered during each of four cocaine exposures during a given experimental session.

Ketoconazole may be administered to a patient by any suitable means, including parenteral, subcutaneous, intrapulmonary, and intranasal administration. Parenteral infusions include intramuscular, intravenous, intraarterial, or intraperitoneal administration. Ketoconazole may also be administered transdermally, for example in the form of a slow-release subcutaneous implant, or orally in the form of capsules, powders, or granules. It may also be administered by inhalation.

Pharmaceutically acceptable carrier preparations for parenteral administration include sterile, aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. The active therapeutic ingredient may be mixed with excipients that are pharmaceutically acceptable and are compatible with the active ingredient. Suitable excipients include water, saline, dextrose, glycerol and ethanol, or combinations thereof. Intravenous vehicles include fluid and nutrient replenishers, electrolyte replenishers, such as those based on Ringer's dextrose, and the like. Preservatives and other additives may also be present such as, for example, antimicrobials, anti-oxidants, chelating agents, inert gases, and the like.

The form may vary depending upon the route of administration. For example, compositions for injection may be provided in the form of an ampule, each containing a unit dose amount, or in the form of a container containing multiple doses.

Ketoconazole may be formulated into therapeutic compositions as pharmaceutically acceptable salts. These salts include the acid addition salts formed with inorganic acids such as, for example, hydrochloric or phosphoric acid, or organic acids such as acetic, oxalic, or tartaric acid, and the like. Salts also include those formed with inorganic bases such as, for example, sodium, potassium, ammonium, calcium or ferric hydroxides, and organic bases such as isopropylamine, trimethylamine, histidine, procaine and the like.

Controlled delivery may be achieved by admixing the active ingredient with appropriate macromolecules, for example, polyesters, polyamino acids, polyvinyl pyrrolidone, ethylenevinylacetate, methylcellulose, carboxymethylcellulose, prolamine sulfate, or lactide/glycolide copolymers. The rate of release of ketoconazole may be controlled by altering the concentration of the macromolecule.

Another method for controlling the duration of action comprises incorporating ketoconazole into particles of a polymeric substance such as a polyester, peptide, hydrogel, polylactide/glycolide copolymer, or ethylenevinylacetate copolymers. Alternatively, ketoconazole may be encapsulated in microcapsules prepared, for example, by coacervation techniques or by interfacial polymerization, for example, by the use of hydroxymethylcellulose or gelatin-microcapsules or poly(methylmethacrylate) microcapsules, respectively, or in a colloid drug delivery system. Colloidal dispersion systems include macromolecule complexes, nanocapsules, microspheres, beads, and lipidbased systems including oil-in-water emulsions, micelles, mixed micelles, and liposomes.

The term "therapeutically effective amount" as used herein refers to an amount of ketoconazole sufficient to significantly decrease the subject's self-administration of cocaine. The term includes, for example, an amount of ketoconazole sufficient to decrease the frequency of cocaine self-administration by at least 10%, and more preferably sufficient to reduce it by 50% to 90%, most preferably 100%. The dosage ranges for the admonistration of ketoconazole are those that produce the desired effect. Generally, the dosage will vary with the age, weight, condition, and sex of the patient, and the extent of the addiction. A person of ordinary skill in the art, given the teachings of the present specification, may readily determine suitable dosage ranges.

In addition, ketoconazole may be used in combination with other drugs known to decrease cocaine self-administration, to lower corticosterone or cortisol concentration, or to bind brain glucocorticoid receptors. While not limiting the scope of the invention, examples of other drugs which may prove especially effective in combination with ketoconazole include mifepristone, metyrapone, etomidate, clotrimazole, aminoglutethimide, and analogues thereof.

While not wishing to be bound by this theory, I believe that ketoconazole decreases self-administration of cocaine both by inhibiting the synthesis of corticosterone or cortisol, and by antagonist binding to the brain glucocorticoid receptors.

The effectiveness of treatment may be monitored by detection methods used in the art, including assays for plasma corticosterone and cocaine concentration, the latter as measured by metabolites in urine.

The following examples are intended to illustrate but not limit the invention. While they are typical of procedures that might be used, other procedures that will readily occur to those skilled in the art may alternatively be used.

Example 1

Experimental Animals

Ten adult male Wistar rats (Harlan Sprague-Dawley) 80 to 100 days old at the start of the experiments were used. These rats were housed singly in cages equipped with a laminar flow unit and air filter in a temperature- and humidity-controlled, AAALAC-accredited animal care facility on a reversed 12 hr light/dark cycle (lights on at 18:00 hr) with free access to water. The rats were maintained at 85 to 90% of their free-feeding body weights by presentations of food pellets (P. J. Noyes, 45 mg) during the behavioral sessions and/or by supplemental post-session feeding (Purina Rat Chow).

Each rat was implanted with a chronic indwelling jugular catheter under pentobarbital anesthesia (50 mg/kg, intraperitoneal ("ip")) with methylatropine nitrate pretreatment (10 mg/kg, ip) using previously reported procedures. Goeders et al., Brain Research, vol. 722, pp. 145–152 (1996). The catheter (0.76 mm o.d.×0.25 mm i.d., polyvinylchloride tubing) was inserted into the right posterior facial vein and pushed down into the jugular vein until it terminated outside the right atrium. The catheter was anchored to tissue in the area and continued subcutaneously to the back, where it exited just posterior to the scapulae through a Marlex mesh®/dental acrylic/22-gauge guide cannula (Plastic Products) assembly that was implanted under the skin for attachment of a leash. The stainless steel spring leash (Plastic Products) was attached to the guide cannula assembly and to a leak-proof fluid swivel suspended above the cage. Tubing connected the swivel to a 20 ml syringe in a motor-driven pump (Razel) located outside the chamber. The swivel and leash assembly was counter-balanced to permit relatively unrestrained movement of the animal. The animals were injected with sterile penicillin G procaine suspension (75,000 units, intramuscular) immediately before surgery, and were allowed a minimum of four days to recover following surgery. The swivel and leash assembly was always connected during the experimental sessions. At the end of each session, the leash was disconnected and a dummy cannula was inserted into the guide before the rats were returned to their home cages. The operation of the catheters was tested weekly. Each rat was injected with methohexital sodium (1.5 mg, intravenous) immediately after the end of an experimental session. An immediate light anesthesia indicated that the catheter was functioning properly.

Experimental Chambers

Standard plastic and stainless steel sound-attenuating operant conditioning chambers (Med-Associates, Inc.) were used for the behavioral experiments. Each experimental chamber was equipped with two response levers (Med-Associates, Inc.) mounted on opposite walls of the chamber. A stimulus light was located above each response lever, and a houselight was centrally mounted at the top of one wall of the chamber. A food pellet dispenser was located beside the food response lever. The chambers were also equipped with an exhaust fan which supplied ventilation and white noise to mask extraneous sounds. An IBM-compatible personal computer and interface system (Med-Associates, Inc.) was used to program the procedures and collect the experimental data.

Training Experimental Animals

Following a minimum of 4 days recovery from surgery, the rats were trained to respond under a multiple, alternating schedule of food reinforcement and cocaine self-administration. During the food component of the schedule, a stimulus light located directly above the food response lever was illuminated to indicate the availability of food reinforcement. Initially, each depression of the food response lever resulted in a brief darkening of the food stimulus light (0.6 sec) and the delivery of a food pellet (45 mg). A 25-sec timeout followed the delivery of each food pellet. During this timeout, the stimulus light was darkened and responses on the food lever were counted but had no scheduled consequences. Responding on the other (cocaine) lever during the food component also had no scheduled consequences. The response requirement for the food lever was gradually increased over several sessions from continuous reinforcement to a fixed-ratio 10 schedule, in which 10 responses were required for food presentation. Following 15 min of access to food, all stimulus lights in the chamber were darkened for a 1-min timeout.

Following the timeout, the stimulus light above the cocaine response lever was illuminated to indicate the availability of cocaine. Initially, each depression of the cocaine response lever resulted in a brief darkening of the stimulus light and an infusion of cocaine (0.25 mg/kg/infusion in 200 μl 0.9% NaCl delivered over 5.6 sec). A 20-sec timeout period followed each infusion. The response requirement for cocaine was gradually increased to a fixed-ratio 4 schedule, in which 4 responses were required for cocaine presentation. After 15 min access to cocaine and a 1-min timeout, the rats were again allowed 15 min access to the food component of the schedule. Access to food and cocaine alternated in this manner every 15 min during the 2-hour behavioral sessions so that each rat was exposed to food and cocaine for four 15-minute periods each.

Each behavioral session began with 15 min access to either food or cocaine, which alternated on a daily basis. Sessions were conducted at the same time each day, Monday through Friday. A stable baseline of responses occurred when the total number of cocaine and food presentations for all 4 exposures, as well as the number of either food or cocaine presentations during each of the 4 exposures, varied less than 10% for 3 consecutive behavioral sessions.

Prior to testing with ketoconazole, the rats were repeatedly exposed to cocaine extinction. On extinction test days, a saline vehicle syringe replaced the 0.25 mg/kg/infusion cocaine syringe normally present, and responses on the "cocaine" lever resulted in infusions of saline. The rats were presented with these saline "extinction probes" on drug test days (Tuesdays and Fridays) until "extinction-like" behavior was observed. Extinction-like behavior was deemed to occur if the total number of responses on the "cocaine" lever was significantly less than baseline and when little or no depression of the "cocaine" lever occurred after the first 15 min exposure to saline.

Ketoconazole Testing

Once consistent and reproducible behavior during cocaine extinction was obtained, ketoconazole testing during cocaine self-administration commenced. Initially, rats were pretreated with varying dosages of ketoconazole (6.25–50 mg/kg, ip) or vehicle, i.e., placebo, (80% propylene glycol and 20% dH$_2$O) 30 min prior to the start of the behavioral session. Each rat was tested with each dose of ketoconazole at least twice in a random order. Ketoconazole was tested on Tuesdays and Fridays, provided that responses had returned to baseline between test days.

Plasma corticosterone was measured following pretreatment with vehicle, and again following pretreatment with 25 mg/kg ketoconazole, a dose that decreased cocaine self-administration without significantly affecting food-reinforced responding. Plasma corticosterone was determined by specific radioimmunoassay using the ImmuChem™ double antibody [$^{125}$I]corticosterone kit (ICN Biomedicals) in tail blood collected immediately following the behavioral sessions using the procedures of Goeders et al., Neuroendocrinology, vol. 64, pp. 337–348 (1996).

Data collected included the total number of infusions and food pellets delivered per session, as well as the number delivered during each of the four presentations of each component of the alternating schedule. The significance of differences between the various treatments was determined by analysis of variance, followed by Tukey's all pairwise comparison procedures; or by a Kruskal-Wallis one-way analysis of variance on ranks, followed by Dunn's comparisons; as appropriate. Plasma corticosterone was expressed as ng/ml. Correlations between the effects of ketoconazole on plasma corticosterone versus the effects of the drug on cocaine self-administration were determined by Spearman's rank order correlation.

Results of Cocaine and Cocaine Extinction Baselines

Figure 2:
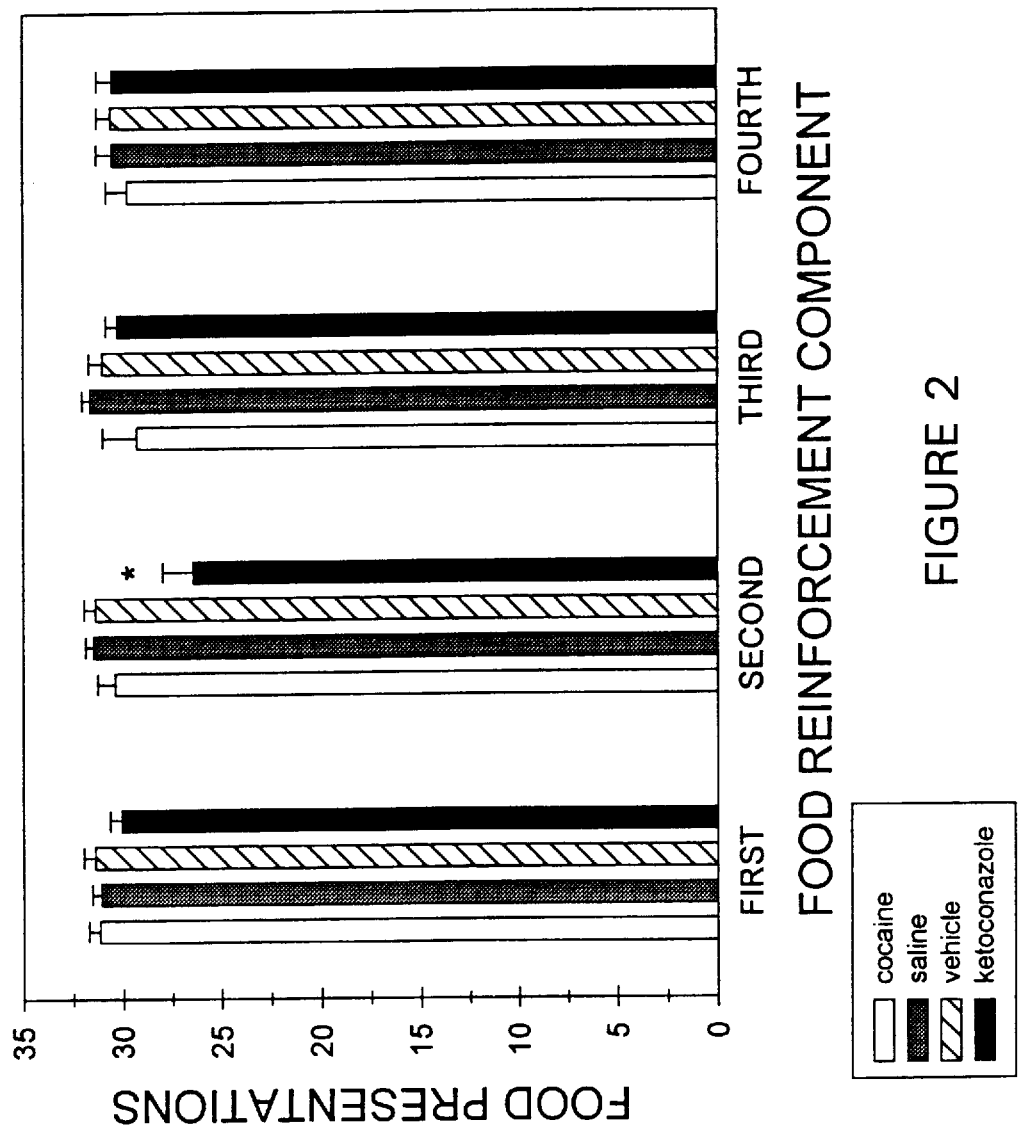
FIG. 2 illustrates the effects of various treatments on the number of food presentations during each of the four food exposures during a given experimental session.

Stable baselines of cocaine—and food—reinforced responses were obtained following approximately 15 to 20 experimental sessions. In general, rats self-administered 8 to 10 cocaine infusions as shown in FIG. 1, and received about 30 food presentations as shown in FIG. 2 during the 4 exposures to each of the two components in the alternating experimental schedule. In both FIGS. 1 and 2, "cocaine" represents the number of infusions delivered when 0.25 mg/kg/infusion cocaine was available. "Saline" shows the effects of substituting saline for cocaine (i.e., cocaine extinction). "Vehicle" shows the effects of the vehicle for ketoconazole (80% propylene glycol and 20% dH$_2$O), administered 30 min prior to the start of the behavioral session. "Ketoconazole" represents the effects of ketoconazole pretreatment (25 mg/kg, ip) delivered 30 min before the start of the session. Significance of the differences was determined with Kruskal-Wallis one-way analysis of variance on ranks, followed by Dunn's comparisons with *p<0.05 for saline vs. cocaine, and for ketoconazole vs vehicle in FIG. 1; and for ketoconazole vs saline in FIG. 2.

Figure 3:
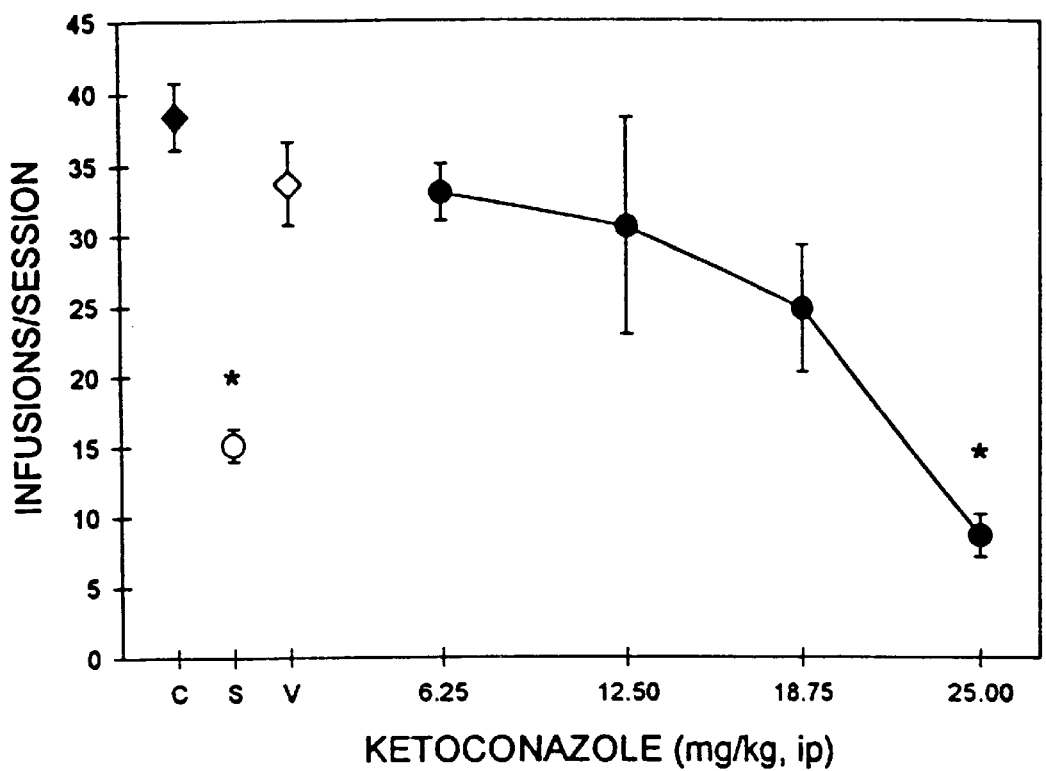
FIG. 3 illustrates the dose-dependent decrease in intravenous cocaine self-administration induced by ketoconazole treatment.

During saline substitution (cocaine extinction), the total number of infusions was significantly less (p<0.05) than that observed during baseline self-administration, as shown in FIG. 3. In FIG. 3, on the x axis, "C" represents the number of infusions delivered when cocaine was available. "S" shows the effects of substituting saline for cocaine (i.e., cocaine extinction). "V" shows the effects of pretreatment with the vehicle for ketoconazole on the number of cocaine infusions. The various doses of ketoconazole, as indicated on the x axis, and vehicle were administered 30 min prior to the start of the behavioral sessions.

FIG. 1 indicates that no significant differences (p=0.095) were found between the number of infusions delivered per session during the first 15 min exposure to cocaine self-administration, and during the first 15 min exposure to saline in cocaine extinction. During extinction training, rats generally sampled at the "cocaine" lever so that the number of infusions during the first exposure was not significantly different from baseline. By contrast, the numbers of infusions delivered during the second (p<0.05), third (p<0.05) and fourth (p<0.05) exposures were significantly reduced during cocaine extinction as compared to baseline.

Results of Pretreatment with Ketoconazole

Pretreatment with ketoconazole resulted in dose-related decreases in cocaine self-administration. Drug intake was significantly less than vehicle (p<0.05), but not significantly different from saline, following the 25 mg/kg dose, as shown in FIG. 3. Numerical decreases were seen at doses of 6.25, 12.5, and 18.75 mg/kg. In this set of experiments, a statistically significant decrease was seen only at 25 mg/kg. At the higher dose of 50 mg/kg ketoconazole, the behavior of the rats slowed following injection of ketoconazole, similar to effects seen with metyrapone (100 mg/kg) in earlier work. (data not shown) Goeders et al., Brain Research, vol. 722, pp. 145–152 (1996).

Similar to the results obtained during the saline cocaine extinction test, FIG. 1 shows no significant differences between drug intake following pretreatment with ketoconazole (25 mg/kg, ip) or with vehicle during the first exposure to cocaine self-administration. However, drug intake following pretreatment with 25 mg/kg ketoconazole was significantly different from vehicle during the second (p<0.05), third (p<0.05) and fourth (p<0.05) exposures to self-administration, but was not significantly different from the results for cocaine extinction for the same exposure periods. Neither cocaine extinction nor pretreatment with ketoconazole (6.25 to 25 mg/kg, ip) affected foodreinforced responses during any of the four exposures to food, as shown in FIG. 2. In fact, the only significant difference in the number of food presentations was that between cocaine extinction and ketoconazole pretreatment during the second exposure (p <0.05). Some of these rats were also tested with a higher dose of ketoconazole (i.e., 50 mg/kg, ip). At this higher dose, both cocaine self-administration and food-reinforced responses were affected. (data not shown) Behavior following ketoconazole pretreatment at a dose of 25 mg/kg was virtually indistinguishable from that obtained during cocaine extinction, showing that ketoconazole specifically attenuated cocaine reinforcement behavior.

Figure 4:
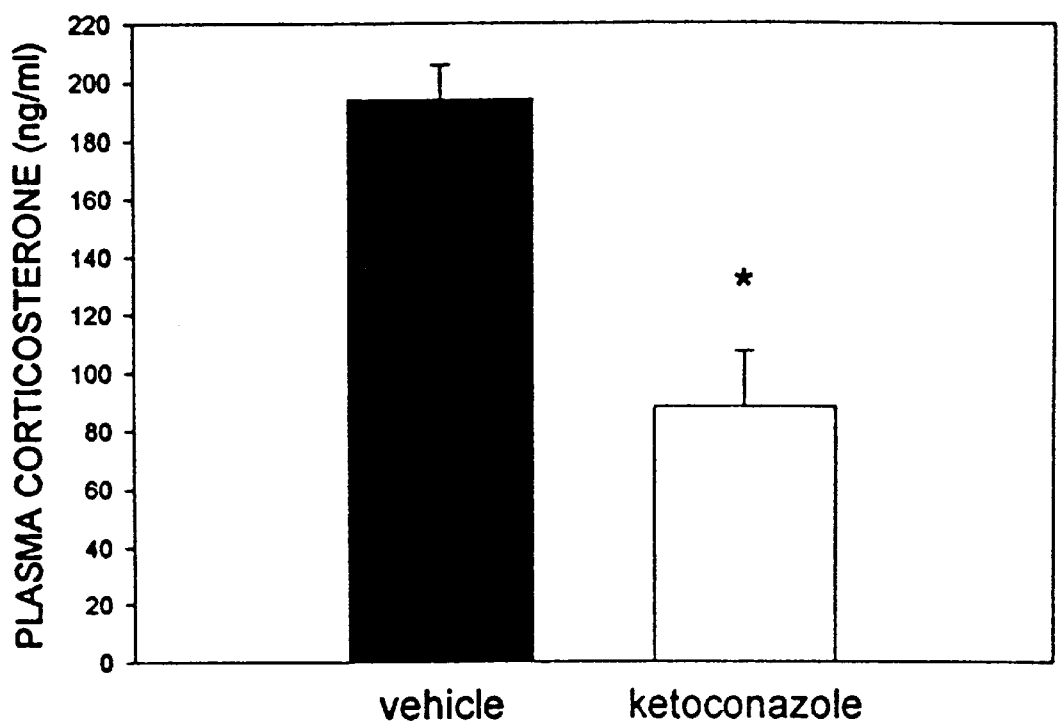
FIG. 4 illustrates the effects of ketoconazole on plasma corticosterone.

Pretreatment with ketoconazole (25 mg/kg, ip) resulted in significant (p<0.05) decreases in plasma corticosterone compared to pretreatment with vehicle, as shown in FIG. 4. In FIG. 4, significance of the difference was determined by analysis of variance, followed by Tukey's all pairwise comparison procedures, with *p<0.05.

Figure 5:
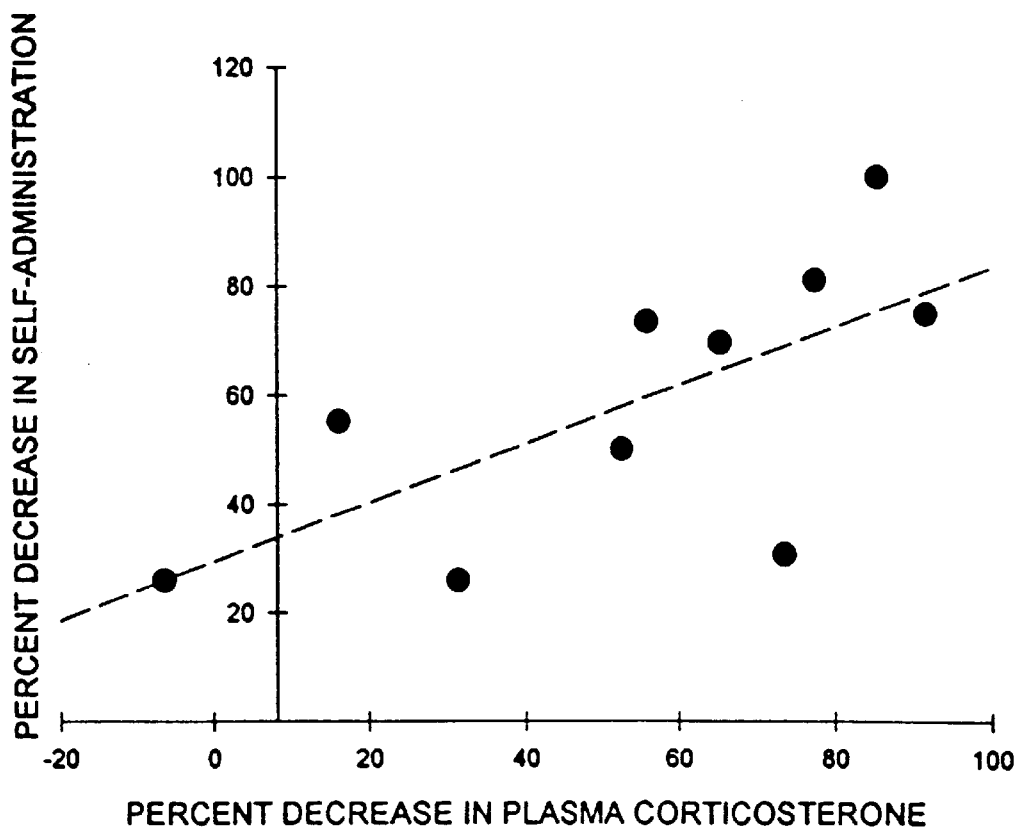
FIG. 5 illustrates the relationship between the effects of ketoconazole injection on plasma corticosterone and on cocaine self-administration, presented as the percent decrease in each as compared to responses to vehicle injection.

When the effects of ketoconazole on cocaine self-administration were plotted as a function of the decrease on plasma corticosterone as in FIG. 5, a significant (p<0.01) positive correlation was observed. The dashed line represents the best fit through the data points. A correlation coefficient (r=0.76) was determined by Spearman's rank order correlation. These data support the theory that the effects of ketoconazole on cocaine self-administration are mediated, at least in part, through effects of the drug on plasma corticosterone.

These experiments demonstrated that ketoconazole decreases intravenous cocaine self-administration in rats at doses that did not affect food-reinforced responses. Rates and patterns of behavior following pretreatment with ketoconazole (25 mg/kg, ip) were very similar to those observed during cocaine extinction, showing that ketoconazole specifically blocked cocaine reinforcement. Plasma corticosterone also decreased significantly following ketoconazole pretreatment. In fact, there was a significant positive correlation between the effects of ketoconazole on cocaine self-administration and the effects of the drug on plasma corticosterone. This indicates that ketoconazole may have reduced drug-intake, at least in part, through its effects on this stress-related hormone. Plasma corticosterone was greater than 150 ng/ml in each rat that eventually self-administered 4 mg of cocaine/hour or more, indicating that plasma corticosterone must be above a critical threshold (e.g., 150 ng/ml) for subsequent low-dose cocaine self-administration to occur. The ketoconazole pretreatment decreased plasma corticosterone below this threshold (i.e., to 88.1±19.2 ng/ml), and subsequent cocaine self-administration was virtually indistinguishable from that observed during cocaine extinction.

Example 2

The effects of ketoconazole were investigated in rats with that had extended experience with cocaine self-administration, but that lacked experience with cocaine extinction. Pretreatment with ketoconazole produced little or no effects on drug-intake. But neither was self-administration altered when cocaine was replaced with saline. These rats continued to press the "cocaine" response lever for an extended number of sessions (i.e., 3 to 5 consecutive sessions, or more) even though these responses only resulted in the presentation of saline. Even though ketoconazole may have completely blocked or reversed cocaine reinforcement to a state analogous to saline delivery, no effects on drugintake were observed; these rats continued to press the lever regardless of whether or not cocaine was available. This experiment indicated the importance of using rats previously exposed to cocaine extinction, because false negative results may otherwise be obtained.

Example 3

Experiments were conducted in rats to determine the effects of exogenous injections of corticosterone and the role of glucocorticoid receptors on the acquisition of intravenous cocaine self-administration. Adult male Wistar rats were tested for self-administration with increasing doses of cocaine (0.0, 0.03125, 0.0625, 0.125, 0.25, 0.5, and 1.0 mg/kg/infusion). Fifteen min prior to each self-administration session, six rats per group were treated daily, with corticosterone (2.0 mg/kg, ip, suspended in saline), or with saline. Daily pretreatment with corticosterone shifted the dose response curve for self-administration; corticosterone-treated rats acquired self-administration at a 0.0625 mg/kg/infusion dose or lower, whereas none of the saline-treated rats acquired this behavior until a 0.125 mg/kg/infusion dose or higher.

To investigate the potential roles of mineralocorticoid (Type I) or glucocorticoid (Type II) receptors on the effects of exogenous corticosterone, separate groups of rats were pretreated daily with the mineralocorticoid agonist aldosterone (0.1 mg/kg, ip, pretreated 15 min prior to test, n=5) or the glucocorticoid agonist dexamethasone (0.1 mg/kg, ip, pretreated 60 min prior to test, n=6). Aldosterone treatment had little to no effect on self-administration. However, dexamethasonetreated rats did not acquire cocaine self-administration at any dose tested, presumably because the relatively high dose of dexamethasone completely inhibited the corticosterone response to cocaine. Experiments will be done to investigate the effects of lower doses of dexamethasone (e.g., 0.01 mg/kg), doses that will not activate the negative feedback processes. These data suggest that the increased sensitivity to cocaine produced by injected corticosterone is due to specific effects of the hormone on glucocorticoid (Type II) receptors.

Without wishing to be bound by this theory, I believe that ketoconazole blocks cocaine craving at lower molar doses than other inhibitors of corticoid synthesis, because ketoconazole acts at two levels: both by blocking glucocorticoid (Type II) receptors so brain cells do not respond to cortisol, and by blocking synthesis of cortisol.

Example 4

Humans trials will be conducted in accordance with applicable laws and regulations. Subjects will be placed in a double-blind, randomized, parallel placebo-controlled study of the effects of orally-administered ketoconazole on cocaine craving and abstinence in 20 patients with cocaine dependency.

The primary objective will be to determine the lowest dose of ketoconazole that will affect cocaine craving and abstinence in outpatients diagnosed with cocaine dependency.

Twenty adult male and female outpatients meeting the inclusion and exclusion criteria will be recruited into this study. These subjects must meet Diagnostic and Statistical Manual IV (DSM IV) criteria for cocaine dependency, and must also test positive for cocaine in a urine drug screen conducted at the initial interview. An initial interview will assess the severity of cocaine dependency using the Addiction Severity Index rating scale. Subjects must be healthy and medically stable, requiring no medications except those for mild hypertension, in which case the subject must be stable for more than 3 months prior to entry into the study. Subjects must also be able to read and write in English and be capable of giving informed consent.

Subjects with a history of hepatitis or with abnormal levels of liver enzymes will be excluded. Also, subjects with a baseline level of cortisol less than 3 βg/dL, or any other clinically significant test abnormality will be excluded.

Following admittance to the study protocol, the subjects will be randomly assigned to placebo or ketoconazole treatment groups. Over the initial 2 weeks of the study (stabilization period), the initial dose of ketoconazole will be increased from 600 mg/day (200 mg three times a day) to 1000 mg/day (200 mg three times a day, 400 mg at bedtime). During stabilization, the subjects must report to the clinic on Mondays and Thursdays for routine blood work (including Chem 20 +Cellular Blood Count and Urine Analysis) as well as a urine drug screen, EKG, and measurement of plasma cortisol. Craving and other psychological tests (Hamilton Anxiety, Beck Depression Index, Addiction Severity Index) will be conducted, as well as an assessment of any side effects. Ketoconazole and placebo medication will also be dispensed on these days.

Following stabilization, the 4-week study will commence. During this study period, the subjects will continue to visit the clinic on Mondays and Thursdays to receive study drug, submit to a urine drug screen and report any side effects. However, blood work and psychological testing will only be conducted on Mondays. After the end of the 4-week study, all medication will be stopped, and the subjects will be asked to return to the clinic for a final follow-up visit.

Subjects' cocaine use will be monitored with the twice weekly urine drug screen and subject reports. Ketoconazole administration may either decrease craving for cocaine, or decrease the subjective effects (e.g., "high", euphoria) of cocaine administration, or both.

Later experiments will test lower doses of ketoconazole. With this theory, it is bound by this theory, it is believed that doses as low as 1 mg/kg/day, including but not limited to 2 mg/kg/day, 3 mg/kg/day, 4 mg/kg/day, 5 mg/kg/day, 6 mg/kg/day, 7 mg/kg/day, and 8 mg/kg/day, will be effective in decreasing the craving for cocaine.

The complete disclosures of all references cited in this specification are hereby incorporated by reference. In the event of an otherwise irreconcilable conflict, however, the present specification shall control. Also incorporated by reference is the complete disclosure of the following paper, which is not prior art to the present invention: Goeders et al., "Ketoconazole Reduces Intravenous Cocaine Self-Administration in Rats," submitted for publication in Psychopharmacology (1997).

I claim:

1. A method of treating a human patient suffering from cocaine addiction, comprising administering to the patient a therapeutically effective amount of ketoconazole.

2. The method of claim 1, additionally comprising the step of administering to the patient a second drug known to decrease the frequency of self-administration of cocaine.

3. The method of claim 2, wherein the second drug is metyrapone.

4. The method of claim 1, additionally comprising the step of administering to the patient a second drug that inhibits the synthesis of glucocorticoids.

5. The method of claim 4, wherein the second drug is selected from the group consisting of metyrapone, etomidate, clotrimazole, aminoglutethimide, and analogues thereof.

6. The method of claim 1, additionally comprising the step of administering to the patient a second drug that binds as an antagonist to brain glucocorticoid (Type II) receptors.

7. The method of claim 6, wherein the second drug is mifepristone.

8. The method of claim 1, wherein said administering of ketoconazole is performed by subcutaneous injection, intravenous injection, oral ingestion, or transdermal absorption.

9. The method of claim 1, wherein the dose of ketoconazole is greater than about 200 mg/day.

10. The method of claim 1, wherein the dose of ketoconazole is about 200 mg/day.

11. The method of claim 1, wherein the dose of ketoconazole is greater than about 600 mg/day.

12. The method of claim 1, wherein the dose of ketoconazole is about 600 mg/day.

13. The method of claim 1, wherein the dose of ketoconazole is about 1 mg/kg/day.

14. The method of claim 1, wherein the dose of ketoconazole is about 2 mg/kg/day.

15. The method of claim 1, wherein the dose of ketoconazole is about 3 mg/kg/day.

16. The method of claim 1, wherein the dose of ketoconazole is about 4 mg/kg/day.

17. The method of claim 1, wherein the dose of ketoconazole is about 5 mg/kg/day.

18. The method of claim 1, wherein the dose of ketoconazole is about 6 mg/kg/day.

19. The method of claim 1, wherein the dose of ketoconazole is about 7 mg/kg/day.

20. The method of claim 1, wherein the dose of ketoconazole is about 8 mg/kg/day.

* * * * *